United States Patent [19]

Sheh

[11] Patent Number: 4,978,783
[45] Date of Patent: Dec. 18, 1990

[54] 2,6-DIMETHOXYHYDROQUINONE-3-MERCAPTOPROPIONIC ACID, 2,6-DIMETHOXYHYDROQUINONE-3-MERCAPTOACETIC ACID, AND ANTITUMOR USE THEREOF

[75] Inventor: Leung Sheh, Taichung, Taiwan

[73] Assignee: National Science Council, Taipei, Taiwan

[21] Appl. No.: 517,714

[22] Filed: May 2, 1990

[51] Int. Cl.$^5$ .................. C07C 149/40; C07C 321/00
[52] U.S. Cl. ................................................ 562/431
[58] Field of Search ........................................ 562/431

[56] References Cited

U.S. PATENT DOCUMENTS

| | | | |
|---|---|---|---|
| 4,067,998 | 1/1978 | Wagner | 562/431 |
| 4,709,049 | 11/1987 | Nagano et al. | 562/431 |
| 4,711,903 | 12/1987 | Mueller et al. | 562/431 |
| 4,755,524 | 7/1988 | Mueller et al. | 562/431 |

FOREIGN PATENT DOCUMENTS 348203 12/1989 European Pat. Off. .

Primary Examiner—Paul J. Killos
Attorney, Agent, or Firm—Bacon & Thomas

[57] ABSTRACT

This invention relates to two novel compounds: 2,6-dimethoxyhydroquinone-3-mercaptopropionic acid and 2,6-dimethoxyhydroquinone-3-mercaptoacetic acid of the formula

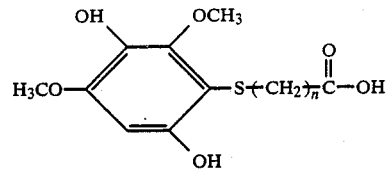

wherein n is an integer of 1 or 2.

3 Claims, No Drawings

2,6-DIMETHOXYHYDROQUINONE-3-MERCAPTOPROPIONIC ACID, 2,6-DIMETHOXYHYDROQUINONE-3-MERCAPTOACETIC ACID, AND ANTITUMOR USE THEREOF

TECHNICAL FIELD OF THE INVENTION

The present invention relates to two novel compounds: 2,6-dimethoxyhydroquinone-3-mercaptopropionic acid and 2,6-dimethoxyhydroquinone-3-mercaptoacetic acid which are potentially useful for the treatment of tumors.

BACKGROUND OF THE INVENTION

D. J. Cosgrove, et al. in their article entitled "Isolation of Methoxy- and 2,6-Dimethoxy-p-benzoquinone from Fermented Wheat Germ" *Nature*, 169, 966 (1952), first reported the isolation of 2,6-dimethoxy-p-benzoquinone (DMQ) from wheat germ.

An Article by R. Pethig, et al. entitled "Ascorbate-quinone interactions: Electrochemical, free radical, and cytotoxic properties" *Proc. Natl. Acad. Sci. USA*, 80, 129–132 (1983), describes that DMQ in combination with L-ascorbic acid is effective for treating Ehrlich ascites-bearing mice.

The compound DMQ has poor solubility in water and has a certain degree of cytotoxicity. Consequently, it will precipitate from the blood easily and will cause destruction of normal cells, rendering it unsuitable for use as an antitumor agent.

An object of the present invention is to introduce the novel 2,6-dimethoxyhydroquinone-3-mercaptopropionic acid and 2,6-dimethoxyhydroquinone-3-mercaptoacetic acid.

Another object of the present invention is to provide a method for inhibiting tumors in mammal by using 2,6-dimethoxyhydroquinone-3-mercaptopropionic acid or 2,6-dimethoxyhydroquinone-3-mercaptoacetic acid in combination with L-ascorbate or D-isoascorbic acid.

SUMMARY OF THE INVENTION

The present invention relates to 2,6-dimethoxyhydroquinone-3-mercaptopropionic acid (DMQ-MP) and 2,6-dimethoxyhydroquinone-3-mercaptoacetic acid (DMQ-MA) compounds of the formula

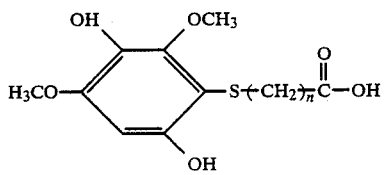

wherein n is an integer of 2 (DMQ-MP) or 1 (DMQ-MA).

The DMQ-MP or DMQ-MA is less cytotoxic and a lot more water-soluble than DMQ. However, when DMQ-MP or DMQ-MA was used in combination with L-ascorbic acid or D-isoascorbic acid, the cytotoxicity to several human cancer cell lines is greatly augmented.

DETAILED DESCRIPTION OF THE INVENTION

The present invention provides the novel 2,6-dimethoxyhydroquinone-3-mercaptopropionic acid (DMQ-MP) and 2,6-dimethoxyhydroquinone-3-mercaptoacetic acid (DMQ-MA) compounds of the formula

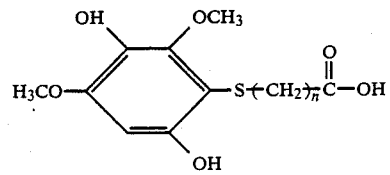

wherein n is an integer of 2 or 1.

DMQ-MP and DMQ-MA both have a significantly improved water-solubility in comparison with DMQ, therefore they may be administrated in solution form without precipitating from the solution. Moreover the accumulation of the drug in human body may be prevented. Besides, DMQ-MP and DMQ-MA retain a certain degree of hydrophobicity to gain passage into the cell via the cell membrane. DMQ-MP or DMQ-MA act synergistically with L-ascorbate or D-isoascorbic acid to give a high cytotoxicity index on several human tumor cell lines in vitro (Table 1-3). The ratio of the concentration of L-ascorbate or D-isoascorbic acid to DMQ-MP or DMQ-MA preferably ranges from 50–100.

DMQ-MP and DMQ-MA can be prepared by the Michael addition process. The reaction product may be purified by medium pressure liquid chromatography followed by crystallization. For example, DMQ-MP may be prepared as follows: 2,6-dimethoxybenzoquinone is dissolved in a mixture of ethanol, water, tetrahydrofuran (THF) and N,N-diisopropylethylamine (DIEA). 3-Mercaptopropionic acid in ethanol is added to the solution and the reaction allowed to proceed at room temperature for 1–3 hours. The resulting product mixture is filtered and the filtrate evaporated to give a crude solid. The product is purified by liquid chromatography to obtain DMQ-MP which crystallized from ether. DMQ-MA can be synthesized and purified by the same procedure except that 3-mercaptopropionic acid is replaced by 2-mercaptoacetic acid.

Details of the present invention can be further understood by the following examples, which are meant to illustrate the present invention and not meant to be limiting.

EXAMPLE 1:

Preparation of 2,6-dimethoxyhydroquinone-3-mercaptopropionic acid (DMQ-MP)

2,6-Dimethoxybenzoquinone (2.0 g) was dissolved in ethanol (95%, 22 ml), water (6 ml), THF (15 ml) and DIEA (1.55 g). 3-mercaptopropionic acid (0.64 g) in ethanol (10 ml) was added in a dropwise fashion within 20 minutes, with stirring and cooling in an ice bath. The reaction was then allowed to proceed at room temperature. After 1.5 hours the reaction medium changed to a deep reddish color. The mixture was filtered and the filtrate evaporated in vacuo to give a solid mixture. This solid mixture was eluted via a silical gel chromatographic column (silica gel 60, [230–400 mesh], Merck) by using $CHCl_3/MeOH/AcOH$ (97:2:1) as the mobile phase. The purified product DMQ-MP was crystallized from ether in a 26.5% yield (0.53 g). Melting point: 113°–115° C. Anal. calcd. for $C_{11}H_{14}SO_6$, C 48.16, H 5.16; Found C 48.16, H 5.17. FABMS (fast atom bombardment mass spectrometry) $[M-H]^-$ (Xe beam) 273.19.

EXAMPLE 2:

Preparation of 2,6-dimethoxyhydroquinone-3-mercaptoacetic acid (DMQ-MA)

The procedures of Example 1 were repeated to prepare DMQ-MA, except that 2-mercaptoacetic acid was used instead of 3-mercaptopropionic acid. The product was crystallized from ether in a 53% yield, m.p. 140°–141° C. Anal. calcd. for $C_{10}H_{12}SO_6$, C 46.15, H 4.65; Found C 46.14, H 4.73. FABMS (Xe beam) [M−H]−259.13.

EXAMPLE 3:

The solubilities of DMQ, DMQ-MP, and DMQ-MA in $H_2O$ at 27° C. are listed as follows:

| | |
|---|---|
| DMQ | 7.4 mg/100 ml |
| DMQ-MP | 533 mg/100 ml |
| DMQ-MA | 500 mg/100 ml |

It can be clearly seen that both DMQ-MP and DMQ-MA have a solubility about 70 times higher than DMQ.

In vitro antitumor assay for DMQ-MP and DMQ-MA

A convenient cytotoxicity assay adopted in this example for the evaluation of antitumor activity is the MTT method disclosed in an article by Twentyman and Luscombe, entitled "A study of some variables in a tetrazolium dye (MTT) based assay for cell growth and chemosensitivity" Br. J. Cancer. 56, 279–285 (1987).

Four different human cancer cell lines were used in this assay. These were KB (oral epidermoid carcinoma); Colo-205 (colon adenocarcinoma); HeLa (cervical carcinoma); and HEP-2 (larynx epidermoid carcinoma).

Cells were taken from exponential phase cultures and were allowed to grow in a plate containing 96 wells using RPMI-1640 medium supplemented with 5% fetal bovine serum, 1 mM glutamine and antibiotics (penicillin and streptomycin) at 37° C. in a $CO_2$ incubator. Cell suspensions were trypsinized and disaggregated. $3 \times 10^3$ cells were inoculated into each well in 0.18 ml of medium, to which 0.02 ml of drug was added. After 4 days of culture, 0.1 mg of 3-(4,5-dimethylthiazol-2-yl)-2,5-diphenyltetrazolium bromide (MTT) was added to each well and the plate incubated for 4 hours. The medium was then removed, 0.2 ml DMSO was added to each well and the plate agitated for 10 min. The optical density of each well was measured at a 545 nm test wavelength and a 690 nm reference wavelength using a Titertek Multiskan plate reader. Absorbance levers from drug tested cells were corrected against untreated control values.

TABLE 1

Cytotoxicity assay of DMQ, DMQ-MP and DMQ-MA against Colo-205 cells by the MTT method

| Drug | Concentration | L-ascorbate | CI* |
|---|---|---|---|
| DMQ | 10 μg/ml | — | 87.9 |
| DMQ | 1.0 μg/ml | 100 μg/ml | 76.6 |
| DMQ-MP | 10 μg/ml | — | 43.5 |
| DMQ-MP | 1.0 μg/ml | 100 μg/ml | 78.2 |
| DMQ-MA | 10 μg/ml | 1.0 μg/ml | 22.1 |
| DMQ-MA | 1.0 μg/ml | 100 μg/ml | 83.7 |

*Cytotoxicity index (CI) = 100% × [1-(O.D. of treated cells / O.D. of control cells)]

The data in Table 1 shows that at a concentration of 10 μg/ml, both DMQ-MP and DMQ-MA have CI values significantly lower than DMQ. Both DMQ-MP and DMQ-MA are highly potent and have cytotoxicity indexes over 78% at a drug concentration of 1.0 μg/ml when L-ascorbate is used as the electron donor at a concentration of 100 μg/ml.

TABLE 2

Cytotoxicity studies of DMQ-MP (1 μg/ml) against four human tumor cell lines under the activation of D-isoascorbic acid (100 μg/ml) by the MTT method

| Drug | Activator | Cell line | CI |
|---|---|---|---|
| — | D-isoascorbic acid | KB | 11 |
| — | D-isoascorbic acid | Colo-205 | 24 |
| — | D-isoascorbic acid | HeLa | 5 |
| — | D-isoascorbic acid | HEP-2 | 13 |
| DMQ-MP | — | KB | 10 |
| DMQ-MP | D-isoascorbic acid | KB | 79 |
| DMQ-MP | — | Colo-205 | 17 |
| DMQ-MP | D-isoascorbic acid | Colo-205 | 78 |
| DMQ-MP | — | HeLa | 11 |
| DMQ-MP | D-isoascorbic acid | HeLa | 88 |
| DMQ-MP | — | HEP-2 | 13 |
| DMQ-MP | D-isoascorbic acid | HEP-2 | 77 |

From the data shown in Table 2, it is clearly seen that either DMQ-MP or D-isoascorbic acid alone has a very low cytotoxicity index (CI) value (<25) against four human tumor cell lines. However, the CI values are synergistically improved to a level of 77–88 when DMQ-MP is used in combination with D-isoascorbic acid.

TABLE 3

Cytotoxicity studies of DMQ-MA (1 μg/ml) against four human tumor cell lines under the activation of L-ascorbate (100 μg/ml) by the MTT method

| Drug | Activator | Cell line | CI |
|---|---|---|---|
| — | L-ascorbate | KB | 0.4 |
| — | L-ascorbate | Colo-205 | 5 |
| — | L-ascorbate | HeLa | 2 |
| — | L-ascorbate | HEP-2 | 9 |
| DMQ-MA | — | KB | 0 |
| DMQ-MA | L-ascorbate | KB | 89 |
| DMQ-MA | — | Colo-205 | 0 |
| DMQ MA | L-ascorbate | Colo-205 | 86 |
| DMQ-MA | — | HeLa | 3 |
| DMQ-MA | L-ascorbate | HeLa | 79 |
| DMQ-MA | — | HEP-2 | 2 |
| DMQ-MA | L-ascorbate | HEP-2 | 86 |

The data in Table 3 shows that DMQ-MA has similar drug potency as DMQ-MP (see Table 2).

It is noteworthy that the concentration of L-ascorbate in the human body can reach 1 mM [P. D. Josephy, B. Palcic, L. D. Skarsgard, "Ascorbate-enhanced cytotoxicity of misonidazole" Nature 271, 370–372 (1978)]. Thus, it is possible to administrate rather high concentrations of L-ascorbate (below 1 mM) either via oral route or by injections.

What is claimed is:

1. A compound of the formula

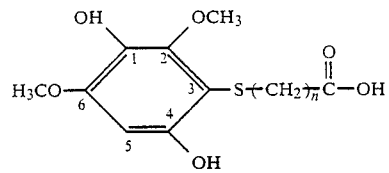

wherein n is an integer of 1 or 2.

2. A pharmaceutical composition for inhibition of tumors which comprises an effective dose of the compound in claim 1, in combination with L-ascorbate or D-isoascorbic acid.

3. A method for inhibiting tumors in mammal which comprises the administration of an effective inhibition dose of the compounds in claim 1, in combination with L-ascorbate acid or D-isoascorbic acid.

* * * * *